United States Patent
Yeke Yazdandoost et al.

(10) Patent No.: US 11,941,907 B2
(45) Date of Patent: Mar. 26, 2024

(54) ACOUSTIC IMAGING SYSTEM ARCHITECTURE

(71) Applicant: Apple Inc., Cupertino, CA (US)

(72) Inventors: Mohammad Yeke Yazdandoost, Santa Clara, CA (US); Giovanni Gozzini, Berkeley, CA (US); Brian Michael King, Saratoga, CA (US); Marcus Yip, San Carlos, CA (US); Marduke Yousefpor, San Jose, CA (US); Ehsan Khajeh, Los Gatos, CA (US); Aaron Tucker, Redwood City, CA (US); Henry H. Yang, Los Gatos, CA (US)

(73) Assignee: Apple Inc., Cupertino, CA (US)

(*) Notice: Subject to any disclaimer, the term of this patent is extended or adjusted under 35 U.S.C. 154(b) by 234 days.

(21) Appl. No.: 17/326,202

(22) Filed: May 20, 2021

(65) Prior Publication Data
US 2021/0271843 A1   Sep. 2, 2021

Related U.S. Application Data

(62) Division of application No. 15/239,455, filed on Aug. 17, 2016, now Pat. No. 11,048,902.
(Continued)

(51) Int. Cl.
*G06V 40/13* (2022.01)
*A61B 5/1172* (2016.01)
*A61B 8/00* (2006.01)

(52) U.S. Cl.
CPC ........ *G06V 40/1306* (2022.01); *A61B 5/1172* (2013.01); *A61B 8/00* (2013.01)

(58) Field of Classification Search
None
See application file for complete search history.

(56) References Cited

U.S. PATENT DOCUMENTS

| 4,729,128 A | 3/1988 | Grimes |
| 5,162,618 A | 11/1992 | Knowles |

(Continued)

FOREIGN PATENT DOCUMENTS

| EA | WO 94/002911 | 2/1994 |
| WO | WO 05/103872 | 11/2005 |

OTHER PUBLICATIONS

Bicz et al., "Ultrasonic sensor for fingerprints recognition," Proceedings of SPIE 2634, Optoelectronic and Electronic Sensors, Jun. 30, 1995, doi: 10-1117/12.213142, 9 pages.
(Continued)

*Primary Examiner* — Hovhannes Baghdasaryan
(74) *Attorney, Agent, or Firm* — Brownstein Hyatt Farber Schreck, LLP

(57) ABSTRACT

An acoustic imaging system includes multiple transducers disposed to circumscribe a portion of substrate. An acoustic imaging system also includes a controller and an image resolver. The transducers convert electrical signals into mechanical energy and/or mechanical energy into electrical signals. The controller is adapted to apply an electrical signal to the transducers which, in response, induce a mechanical wave, such as a surface wave, into the circumscribed portion. The controller is also adapted to receive electrical signals from the transducers. The image resolver uses the electrical signals received by the controller in order to construct an image of an object in physical contact with the substrate.

18 Claims, 10 Drawing Sheets

Related U.S. Application Data

(60) Provisional application No. 62/207,589, filed on Aug. 20, 2015.

(56) References Cited

U.S. PATENT DOCUMENTS

| | | | |
|---|---|---|---|
| 5,381,696 A | 1/1995 | Ichinose et al. |
| 5,515,298 A | 5/1996 | Bicz |
| 5,589,636 A | 12/1996 | Bicz |
| 5,719,950 A | 2/1998 | Osten |
| 5,886,452 A | 3/1999 | Toda |
| 6,091,406 A | 7/2000 | Kambara |
| 6,159,149 A | 12/2000 | Erikson |
| 6,164,135 A | 12/2000 | Bicz |
| 6,720,712 B2 | 4/2004 | Scott |
| 7,032,454 B2 | 4/2006 | Amano |
| 7,400,750 B2 | 7/2008 | Nam |
| 7,449,821 B2 | 11/2008 | Dausch |
| 7,458,268 B2 | 12/2008 | Schneider et al. |
| 7,497,120 B2 | 3/2009 | Schneider et al. |
| 7,568,391 B2 | 8/2009 | Schneider et al. |
| 7,656,932 B2 | 2/2010 | Durand |
| 7,667,374 B2 | 2/2010 | Aono et al. |
| 7,734,435 B2 | 6/2010 | Thomas et al. |
| 7,739,912 B2 | 6/2010 | Schneider et al. |
| 7,770,456 B2 | 8/2010 | Stevenson et al. |
| 8,047,995 B2 | 11/2011 | Wakabayashi et al. |
| 8,054,203 B2 | 11/2011 | Breed et al. |
| 8,085,998 B2 | 12/2011 | Setlak et al. |
| 8,095,328 B2 | 1/2012 | Thomas et al. |
| 8,179,678 B2 | 5/2012 | Yamashita et al. |
| 8,201,739 B2 | 6/2012 | Schneider et al. |
| 8,335,356 B2 | 12/2012 | Schmitt |
| 8,345,508 B2 | 1/2013 | Wodnicki et al. |
| 8,508,103 B2 | 8/2013 | Schmitt et al. |
| 8,536,465 B2 | 9/2013 | Hagiwara et al. |
| 8,576,202 B2 | 11/2013 | Tanaka et al. |
| 8,601,876 B2 | 12/2013 | Schneider et al. |
| 8,617,078 B2 | 12/2013 | Machida et al. |
| 8,666,126 B2 | 3/2014 | Lee et al. |
| 8,692,812 B2 | 4/2014 | Hecht |
| 8,724,859 B2 | 5/2014 | Schneider et al. |
| 8,743,091 B2 | 6/2014 | Bernstein |
| 8,781,180 B2 | 7/2014 | Schneider et al. |
| 8,791,792 B2 | 7/2014 | Benkley, III |
| 8,982,089 B2 | 3/2015 | Lim |
| 9,044,171 B2 | 6/2015 | Venkatraman et al. |
| 9,056,082 B2 | 6/2015 | Liautaud et al. |
| 9,100,034 B2 | 8/2015 | Oshima |
| 9,132,693 B2 | 9/2015 | Klootwijk et al. |
| 9,170,668 B2 | 10/2015 | Schneider et al. |
| 9,201,546 B2 | 12/2015 | Son et al. |
| 9,275,625 B2 | 3/2016 | Kim et al. |
| 9,323,393 B2 | 4/2016 | Djordjev et al. |
| 9,360,365 B2 | 6/2016 | Tsuchimoto |
| 9,465,972 B2 | 10/2016 | Chung et al. |
| 9,568,315 B2 | 2/2017 | Naoka, II et al. |
| 9,582,705 B2 | 2/2017 | Du et al. |
| 9,597,014 B2 | 3/2017 | Venkatraman et al. |
| 9,607,203 B1 | 3/2017 | Yazdandoost et al. |
| 9,613,246 B1 | 4/2017 | Gozzini et al. |
| 9,747,988 B2 | 8/2017 | Yazdandoost et al. |
| 9,750,451 B2 | 9/2017 | Masson et al. |
| 9,778,193 B2 | 10/2017 | Vacca |
| 9,824,254 B1 | 11/2017 | Yazdandoost et al. |
| 9,857,872 B2 | 1/2018 | Terlizzi et al. |
| 9,904,836 B2 | 2/2018 | Yazdandoost et al. |
| 9,927,926 B2 | 3/2018 | Peng |
| 9,952,095 B1 | 4/2018 | Hotelling et al. |
| 9,979,955 B1 | 5/2018 | Guo |
| 9,984,271 B1 | 5/2018 | King et al. |
| 10,036,734 B2 | 7/2018 | Fennell et al. |
| 10,061,963 B2 | 8/2018 | Yazdandoost et al. |
| 10,133,904 B2 | 11/2018 | Yazdandoost et al. |
| 10,198,610 B1 | 2/2019 | Yousefpor et al. |
| 10,203,816 B2 | 2/2019 | Nelson et al. |
| 10,217,045 B2 | 2/2019 | Lal et al. |
| 10,241,223 B2 | 3/2019 | Jin et al. |
| 10,275,633 B1 | 4/2019 | Yousefpor et al. |
| 10,275,638 B1 | 4/2019 | Yousefpor et al. |
| 10,324,065 B2 | 6/2019 | Lee et al. |
| 10,325,136 B1 | 6/2019 | Yeke Yazdandoost et al. |
| 10,366,269 B2 | 7/2019 | Lu et al. |
| 10,430,631 B2 | 10/2019 | Lu et al. |
| 10,503,948 B2 | 12/2019 | Kitchens, II et al. |
| 10,713,823 B2 | 7/2020 | Teshigawara et al. |
| 11,009,390 B2 | 5/2021 | Hotelling et al. |
| 2003/0102777 A1 | 6/2003 | Kuniyasu et al. |
| 2003/0109993 A1 | 6/2003 | Peat et al. |
| 2004/0140735 A1 | 7/2004 | Scott et al. |
| 2004/0264746 A1 | 12/2004 | Polcha et al. |
| 2006/0196271 A1 | 9/2006 | Jancsik et al. |
| 2008/0142571 A1 | 6/2008 | Yokozuka et al. |
| 2008/0175450 A1 | 7/2008 | Scott |
| 2012/0092026 A1 | 4/2012 | Liautaud et al. |
| 2013/0278111 A1 | 10/2013 | Sammoura et al. |
| 2014/0359757 A1 | 12/2014 | Sezan et al. |
| 2015/0053006 A1 | 2/2015 | DeCoux et al. |
| 2015/0358740 A1 | 12/2015 | Tsai et al. |
| 2016/0246396 A1 | 8/2016 | Dickinson et al. |
| 2017/0053151 A1 | 2/2017 | Yazdandoost et al. |

OTHER PUBLICATIONS

Gumienny et al., "Synthetic aperture acoustic microscope for evaluation of finger tip peripheral skin structure," Proceedings of SPIE, Optical Biophysics, Mar. 30, 1995, doi: 10.1117/12.205999, 5 pages.

Definition of Generate, Merriam-Webster, https://www.merriam-webster.com/dictionary/generate, retrieved Dec. 28, 2020, 2 pages.

ACOUSTIC IMAGING SYSTEM ARCHITECTURE

CROSS-REFERENCE TO RELATED APPLICATIONS

This application is a division of U.S. patent application Ser. No. 15/239,455, filed Aug. 17, 2016, which is a nonprovisional of, and claims the benefit under 35 U.S.C. 119(e) of, U.S. Provisional Patent Application No. 62/207,589, filed Aug. 20, 2015, the disclosures of which are hereby incorporated herein by reference in their entirety.

FIELD

This disclosure relates generally to imaging systems, and more particularly, to systems and methods for operating an acoustic imaging system as a biometric sensor associated with a display of an electronic device.

BACKGROUND

An electronic device can include a biometric sensor, such as a fingerprint sensor, to establish an identity of an unknown user prior to performing a task. The fingerprint sensor obtains an image of a fingerprint of the user and compares information derived from that image to information stored in a protected database accessible to the electronic device. The task is performed by the electronic device only after the comparison results in an affirmative match.

A conventional fingerprint sensor includes an array of capacitive sensors positioned below a dielectric material that may be touched by a user. The resolution of the fingerprint sensor is bounded, among other things, by the number of capacitive sensors within the array, the physical size of each capacitive sensor, and the integration time required to sample each capacitive sensor. In addition, capacitive sensors are typically optically opaque; it may be difficult to incorporate a conventional fingerprint sensor into a display of an electronic device.

SUMMARY

Embodiments described herein reference an acoustic imaging sensor incorporating a distribution of transducers disposed to circumscribe a portion of a substrate. In one example, the substrate is a transparent cover of a display an electronic device formed from glass, sapphire, or another optically transparent material. In this example, the distribution of transducers may be hidden by a bezel of the display.

In one example, each transducer is operated in one or more modes, such as a drive mode and a sense mode. When in the drive mode, a transducer mechanically deforms in response to a drive signal. When in the sense mode, a transducer produces an electrical signal in response to a mechanical deformation. A transducer is mechanically deformed as a result of a mechanical wave such as a surface wave, shear wave, plane wave, or other acoustic wave type that propagates through a top surface and/or through the thickness of the substrate.

The acoustic imaging sensor also includes a controller configured to generate an ultrasonic wave within, or on a top surface of, the substrate and, separately, to receive acoustic reflections resulting therefrom. An acoustic reflection is generated by an acoustic impedance mismatch resulting from an object engaging the top surface of the substrate. In one example, the object engaging the top surface of the substrate is user's finger.

The controller generates an ultrasonic wave by generating and applying a drive signal to one or more of the transducers, operating these elements in the drive mode. Thereafter, the controller operates at least one of the transducers in the sense mode to receive one or more electrical signals generated by the transducers.

The acoustic imaging sensor also includes an image resolver configured to, based on the one or more electrical signals received by the controller, construct an image, either partial or complete, of an object (if any) engaging the top surface of the substrate.

In one embodiment, the transducers are disposed as rows adjacent the perimeter of the circumscribed portion of the substrate.

BRIEF DESCRIPTION OF THE DRAWINGS

Reference will now be made to representative embodiments illustrated in the accompanying figures. It should be understood that the following descriptions are not intended to limit the disclosure to one preferred embodiment. To the contrary, each is intended to cover alternatives, modifications, and equivalents as may be included within the spirit and scope of the described embodiments as defined by the appended claims.

The use of the same or similar reference numerals in different drawings indicates similar, related, or identical items where appropriate.

Figure 1:
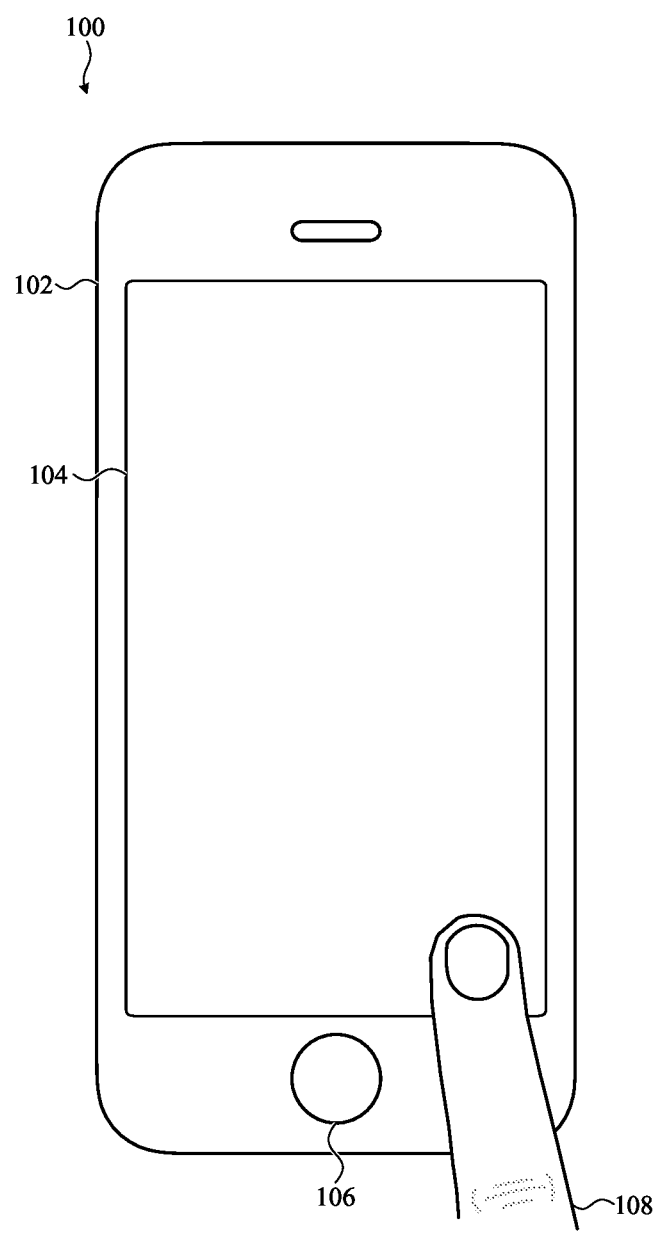
FIG. 1 depicts an example electronic device that can include an acoustic imaging system within a display.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Embodiments described herein generally reference an electronic device that incorporates an acoustic imaging system operated in conjunction with an input-responsive display of the electronic device.

In many examples, the acoustic imaging system is configured to resolve an image of a user's fingerprint when the user touches the display. The acoustic imaging system operates by generating acoustic waves (or pulses) that propagate through an external surface of the display and thereafter monitoring reflections, attenuations, and/or diffractions to those acoustic waves caused by the user's fingerprint. After the user touches the display, and after a fingerprint image is resolved by the system, a processor in communication with the system compares the resolved image—or information derived therefrom—to entries in a database of previously-stored fingerprint images or data. If the processor determines a match, the processor informs the electronic device, after which the electronic device can perform a restricted-access task, such as showing private, personal, or confidential information on the display (e.g., bank statements, health information, communications, corporate or business information, trade secrets, and so on).

As used herein, the term "image" and the phrase "resolved image" typically refer to a two-dimensional collection of pixels, the coordinates of which correspond to local acoustic characteristics (e.g., reflectivity, transmittance, absorption, diffraction characteristics, and so on) of the input-responsive surface that may change when an object, such as a user's finger, is placed in contact with the surface at that location. The total area over which an object contacts the substrate is referred to herein as the "contact area."

As noted above, the surface is typically an input-responsive surface of an electronic device such as, but not limited to: a touch-sensitive surface, a touch-sensitive display, a force-sensitive surface, a force-sensitive display, an exterior surface of a housing or enclosure such as a protective outer layer, and so on.

For simplicity of description, the embodiments that follow are described in reference to an acoustic imaging system associated with a touch and/or force input-responsive display of a portable electronic device. However, such a configuration is not required; an acoustic imaging system such as described herein (or a portion thereof) can be implemented in any suitable or implementation-specific manner and incorporated into any suitable electronic device or electronic device system including, but not limited to, wearable electronic devices, laptop devices, tablet devices, desktop devices, automotive or aeronautical information or entertainment systems, gaming devices, home or commercial appliances, industrial control devices, and so on.

Typically, an acoustic imaging system as described herein includes several acoustic transducers coupled to the input-responsive substrate. In certain implementations, the system also includes a controller and an image resolver. The transducers convert electrical signals into mechanical energy and, similarly, mechanical energy into electrical signals. The controller is adapted to apply an electrical signal to the transducers which, in response, generate a mechanical wave in the substrate. This operation is referred to herein as "driving" the transducers. Transducers can be driven individually, simultaneously, or with a particular timing pattern.

An object in physical contact with the substrate, such as a ridge of a fingerprint, introduces an acoustic impedance mismatch boundary that causes one or more mechanical waves—generated during one or more drive operations—to reflect, diffract, and/or attenuate. The controller is adapted to receive electrical signals generated by the transducers in response to those reflections, diffractions, and attenuations. This operation is referred to herein as "sensing" or "reading" the transducers. Thereafter, the image resolver obtains the electrical signals read by the controller and constructs an approximated map or image of the object in contact with the substrate.

These and other embodiments are discussed below with reference to FIGS. 1-5. However, those skilled in the art will readily appreciate that the detailed description given herein with respect to these figures is for explanatory purposes only and should not be construed as limiting.

FIG. 1 depicts an example electronic device that can include an acoustic imaging system such as described herein. In the illustrated example, the electronic device 100 is implemented as a portable electronic device such as a cellular phone, although such a form factor may not be required.

The electronic device 100 includes a housing 102 and a display 104. The display 104 is disposed below a cover configured to protect the display 104. In many cases, the cover can be formed from an optically transparent and mechanically rigid material such as glass, sapphire, polycarbonate, and the like.

In many examples, the display 104 includes one or more of a variety of display elements or layers. For example, the display 104 may include a liquid crystal display, a thin film transistor display, an organic light emitting diode display, organic electroluminescence display, or other type of display. The display 104 may be used to present visual information to the user and may be operated in accordance with one or more display modes or the software applications being executed on the electronic device 100. In many cases, the display 104 can include or operate in conjunction with one or more input devices. For example, the display 104 may be configured to receive touch, gesture, and/or force input.

The electronic device 100 can also include one or more input elements such as a button 106. The button 106 may be a physical button such as a push button or switch. In other examples, the button 106 can be a touch input device that does not physically depress such as a capacitive button. In other cases, the button 106 can be a virtual button shown on the display 104.

In many embodiments, an acoustic imaging system (not shown) is disposed within the housing 102 of the electronic device 100 and coupled to the cover of the display 104. The acoustic imaging system is configured to obtain an image of an object, such as the pad of a finger (e.g., fingerprint) of a user 108, in physical contact with the cover.

In one example, the acoustic imaging system is positioned around the perimeter of a portion of the cover that may regularly receive touch input of a user 108, such as a bottom portion of the cover adjacent the button 106. In this manner, each time (or at selected times based on operational modes of the electronic device 100) the user 108 presses a bottom portion of the display 104, the acoustic imaging system can be used to resolve an image of a fingerprint of the user 108. In other cases, more than one fingerprint image can be resolved at the same time.

In another example, the acoustic imaging system is positioned around the entire perimeter of the display 104. In this manner, each time the user 108 presses any portion of the display 104, the acoustic imaging system can be used to resolve an image of a fingerprint of the user 108.

In other examples, the acoustic imaging system is positioned adjacent a non-display portion of the electronic device 100. For example, the acoustic imaging system can be positioned around the perimeter of a cap of the button 106. The acoustic imaging system depresses with the button 106. In this manner, each time the user 108 presses the button 106, the acoustic imaging system can be used to map a fingerprint of the user 108.

In yet another example, the acoustic imaging system is positioned adjacent a non-input portion of the electronic device 100. For example, the acoustic imaging system can be within or coupled to the housing 102 of the electronic device 100. In this manner, each time the user 108 holds the electronic device 100 in the user's hand, the acoustic imaging system can be used to map a fingerprint or handprint of the user 108.

Once an image of fingerprint (or other biometrically-unique surface characteristics such as handprints, ear prints, and so on) of the user 108 is mapped by the acoustic imaging system, the obtained image (and/or data derived therefrom, such as the output of a mathematical function such as a hashing function) can be compared to a database of known images or data to determine if the obtained image matches a known image. If an affirmative match is obtained, the electronic device 100 can perform a function or task related to the match. In one example, the electronic device 100 performs an authenticated function, such as displaying financial information or trade secret information on the display 104.

In another example, an acoustic imaging system can be configured to map the biometrically-unique features of a user's ear (e.g., size, shape, skin patterns, and so on) each time the user raises the electronic device 100 to the user's ear. In another example, an acoustic imaging system can be configured to map the biometrically-unique features of a user's hand print (e.g., skin patterns, scar patterns, and so on) each time the user grasps the electronic device 100 in the user's hand. In some cases, the electronic device can respond differently if the electronic device determines that it is being held by the user 108 in the user's left or right hand.

Figure 2:
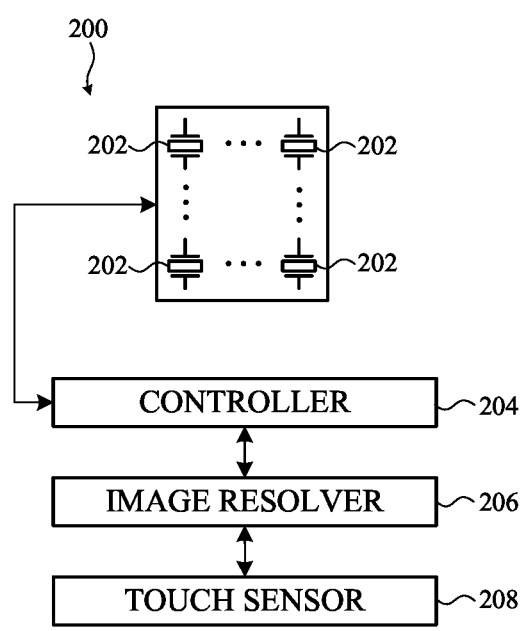
FIG. 2 depicts a simplified block diagram of an acoustic imaging system.

FIG. 2 depicts a simplified block diagram of an acoustic imaging system. The acoustic imaging system 200 includes a distribution of transducers 202 arranged in a rectangular configuration. Each transducer of the distribution of transducers 202 contract or expand in response to an electrical signal supplied by a controller 204. In many examples, the transducers are formed with a piezoelectric material as lead zirconate titinate, zinc oxide, aluminum nitride, potassium niobate, bismuth titinate, or any other piezoelectric material.

The transducers can be coupled to a rigid substrate (not shown), such as the cover of the display 104 of the electronic device 100 as shown in FIG. 1. In another example, the transducers can be coupled to a support or a frame within the electronic device 100.

In many examples, the transducers are arranged to circumscribe an interior portion of the substrate. For example, the distribution of transducers 202 can circumscribe a rectangular area. In this manner, the distribution of transducers 202 follows the periphery or perimeter of the circumscribed portion. In other cases, the distribution of transducers 202 can circumscribe a different area, such as a square, circular, polygonal, or arbitrarily-shaped area. In many cases, the transducers are formed onto a top or bottom surface of the substrate nearby the substrate's edge, although this is not required.

In many embodiments, the transducers are configured for both inducing and detecting mechanical waves (e.g., shear waves, surface waves, longitudinal waves, transverse waves, and so on) in or on the substrate. In other words, a transducer can be operated in more than one mode. A transducer operated in a drive mode generates a mechanical wave in the substrate in response to an electrical signal from the controller 204. The same transducer operated in a sense mode generates an electrical signal in response to a mechanical wave within the substrate.

In other embodiments, certain transducers of the distribution of transducers 202 can be configured to operate in only a drive mode or a sense mode. A drive transducer can be paired with, or positioned adjacent to, a sense transducer. In one example, a row of drive transducers is positioned adjacent a row of sense transducers. Other implementation-specific configurations, groups, and arrangements of drive transducers and sense transducers can be used in particular embodiments.

The controller 204 is configured to provide electrical energy in the form of an electrical signal (e.g., impulse, square wave, triangular wave, sine wave, or other waveform) to each transducer of the distribution of transducers 202. In some cases, a transducer may be configured to resonate at a particular frequency, but this may not be required.

In one example, the controller 204 can provide a first voltage to a first transducer and a second voltage to a second transducer. In addition, the controller 204 can control the duration and magnitude of the voltage applied to each independent transducer of the one or more transducers. In some cases, the controller 204 applies the same electrical signal to each transducer simultaneously.

In one embodiment, the controller 204 applies an electrical signal to groups or sets of transducers. For example, if the distribution of transducers 202 are arranged to circumscribe a rectangular area, the controller 204 can apply an electrical signal the group of transducers forming a top edge of the rectangular area. Thereafter, the controller 204 can apply an electrical signal to the group of transducers forming a right edge, left edge, or bottom edge of the rectangular area. In other cases, alternating transducers can be driven at the same time.

The controller 204 can also operate in one or more modes. In certain embodiments, the controller 204 is operated in an integration mode. Herein, the term "integration mode" refers to a controller mode in which the controller provides electrical energy (e.g., drives) to one or more transducers.

When in the integration mode, the controller 204 is configured to provide electrical energy in the form of an electrical signal to one or more of the transducers of the distribution of transducers 202. In response, the transducers produce an acoustic output in the form of a mechanical wave within the substrate, directed inwardly toward the circumscribed portion. In many embodiments, the electrical energy provided by the controller 204 is an abbreviated electrical pulse that induces a mechanical wave in the substrate. In many cases, the controller 204, in an integration mode, induces the transducers to generate a substantially longitudinal and/or planar mechanical wave with minimal transverse components (e.g., pressure pulse, surface wave, or pulse wave).

As noted above, the controller 204 can apply an electrical signal to groups of transducers. In this case, the controller 204, in an integration mode, induces a selected group of transducers to generate a substantially longitudinal and/or planar mechanical wave, with minimal transverse components, that traverses the substrate substantially parallel to the group. For example, if the distribution of transducers 202 are arranged to circumscribe a rectangular area, the controller 204 can apply an electrical signal the group of transducers forming a top edge of the rectangular area, which, in turn, induces a substantially longitudinal and/or planar mechanical wave that traverses the rectangular area toward a bottom edge thereof. Similarly, the controller 204 can induce a mechanical wave that traverses the rectangular area from a right edge to a left edge, from a left edge to a right edge, and from a bottom edge to a top edge.

In still other examples, the controller 204 can induce a mechanical wave from a portion of one edge, or a mechanical wave that traverses the circumscribed portion at an angle. For example, a controller 204 can induce a mechanical wave to traverse the circumscribed portion from a right edge of the circumscribed portion to the top edge of the circumscribed portion.

Operations in which substantially longitudinal and/or planar mechanical waves are induced to traverse a circumscribed portion of a surface from one edge to another are typically referred to herein as "scanning" operations.

In other embodiments, in an integration mode, the controller 204 can apply an electrical signal to an individual transducer. More generally, the controller 204 can apply an electrical signal to a single transducer, a group of transducers, a line of transducers, all transducers, a pattern of transducers, and so on. The controller 204 may (in the integration mode), in some embodiments, apply the electrical signal(s) at different times to induce different mechanical waves within the substrate. For example, the controller 204 can be configured to induce a plane wave, a series of plane waves, an angular wave, a patterned wave, or any other suitable wave or waves.

After producing the mechanical wave or waves within the substrate with one or more transducers, the controller 204 can transition into a receiving mode. In a receiving mode, the controller 204 couples to one or more transducers, sampling electrical signals generated thereby over a period of time. In many cases, the controller 204 transitions to the receiving mode immediately after generating the mechanical wave in the integration mode. For example, the controller 204 (in the integration mode) can apply an electrical signal to a single transducer, after which the same transducer and/or other transducer(s) adjacent to or separated from that transducer can be monitored by the controller 204 (in the receiving mode) for electrical signals generated in response to received acoustic reflections, diffractions, or attenuations.

As with the integration mode, the controller 204 can couple to individual transducers or groups of transducers in the receiving mode. Continuing the example presented above, if the distribution of transducers 202 are arranged to circumscribe a rectangular area, and the controller 204 initiates a scan from a top edge of the rectangular area, the controller 204 can monitor for electrical signals from the transducers associated with a bottom edge, a right edge, or a left edge of the rectangular area. In other cases, other transducers, groups of transducers, or all transducers together can be monitored when the controller 204 is in the receiving mode. In one embodiment, a reflection of a mechanical wave induced by a single transducer within the top edge is received by one or more transducers at the top edge.

An image resolver 206 communicates with the controller 204. The image resolver obtains the electrical signals received by the controller 204 in the receiving mode. If an object is not in physical contact with the substrate, the mechanical wave is not perturbed and only minimal, if any, reflection, diffraction, or attenuation the energy of the mechanical wave occurs as the wave traverses of the circumscribed portion of the substrate.

Alternatively, if an object, such as a finger, is in physical contact with the substrate, one or more acoustic impedance mismatch boundaries are introduced that cause the mechanical wave generated during a drive operation (e.g., integration mode of the controller 204) to reflect, diffract, or attenuate the energy of that mechanical wave. The image resolver 206 constructs an approximated map (e.g., image) of the object by analyzing the signals received by the controller 204. In many cases, the image resolver 206 employs a spatial filtering technique to generate approximated image of the object in contact with the substrate.

In one example, information obtained by the image resolver 206 can be collected over multiple integration and receiving mode operations. In one example, the controller 204 can initiate a scan operation from a top edge to a bottom edge of a rectangular area. Immediately after the mechanical wave begins propagating from the top edge, all transducers may be monitored by the controller 204, now in a receiving mode. Data streams from each transducer are cached by the image resolver 206 until all reflections, attenuations, or diffractions resulting from the scan operation can be received (e.g., the maximum travel time for the mechanical wave to reach the bottom edge of the rectangular area, reflect, and traverse the substrate to reach the top edge of the rectangular area).

Next, the controller 204 can initiate a scan operation from the bottom edge to the top edge. Immediately after the mechanical wave begins propagating from the bottom edge, all transducers may be monitored by the controller 204. Data from each transducer is cached by the image resolver 206 until the scan operation completes. In the same manner, the image resolver 206 can cache data obtained from scan operations traversing from a right edge to a left edge and from a left edge to a right edge. In this example, after the four scan operations are completed, the image resolver 206 can begin generating the image of the object in contact with the substrate.

In many cases, the image resolver 206 is also coupled to a touch sensor 208 that is configured to detect the location and area of a touch on the substrate. In these examples, the image resolver 206 can use information about the area, orientation, and size of the touch to inform the generation of the image of the object in contact with the substrate. In some cases, the touch sensor 208 is configured to provide force information as well which can be additionally used by the image resolver 206.

In many embodiments, the image resolver 206 and the controller 204 are implemented as separate components of the acoustic imaging system 200, although such a configuration is not required. For example, in one embodiment the image resolver 206 and the controller 204 are subcomponents of a single component, such as instructions or subroutines executed by a processor.

Figure 3A:
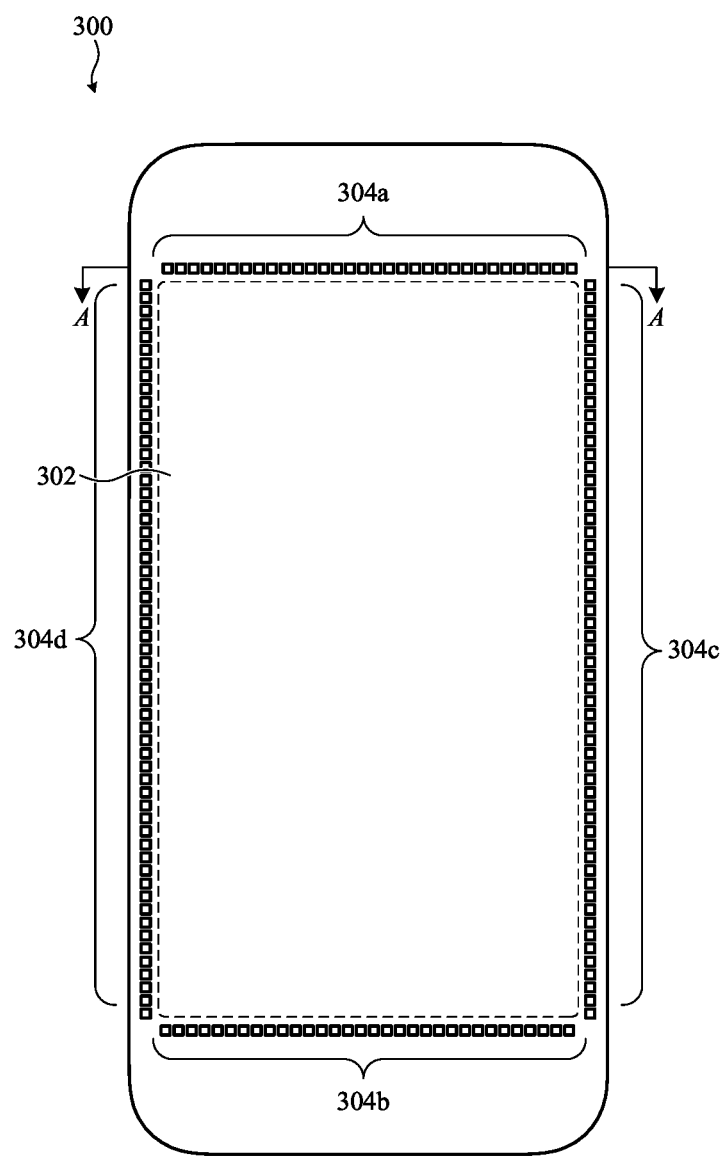
FIG. 3A depicts a distribution of transducers associated with an acoustic imaging system disposed on a bottom surface of a cover so as to circumscribe a substantially rectangular area.

FIG. 3A depicts one example distribution of transducers associated with an acoustic imaging system disposed on a bottom surface of a cover 300 so as to circumscribe a substantially rectangular area. The cover 300 forms a portion of an external surface of an electronic device, such as the electronic device 100 depicted in FIG. 1.

The cover 300 can take substantially any shape appropriate for a particular implementation. As illustrated, the cover 300 is a rounded rectangle. The cover 300 is formed from a rigid material such as strengthened glass or sapphire. The rigidity of the cover 300 serves to protect the internal components of an electronic device onto which the cover 300 is disposed. More particularly, the cover 300 may be disposed over a display of the electronic device.

A number of transducers can be distributed on the bottom surface of the cover 300. The transducers circumscribe a circumscribed portion 302. The circumscribed portion 302 is approximately equal to the area of a display that the cover 300 is configured to protect. In many cases, the circumscribed portion 302 of the cover 300 is transparent, whereas the remainder of the cover 300 (e.g., bezel) is opaque. The opaque portions of the cover 300 hide the transducers from view.

The transducers are disposed around the circumscribed portion 302 in four separate linear groups (e.g., rows and/or columns). A top edge group 304a, a bottom edge group 304b, a right edge group 304c, and a left edge group 304d.

As noted with respect to other embodiments described herein, the transducers can be formed directly onto the bottom surface of the cover 300. In other examples, the transducers can be adhered to the bottom surface of the cover 300. In yet other examples, the transducers are disposed at least partially within the cover 300.

Also as noted with respect to other embodiments described herein, the transducers can be operated in one or more modes. For example, the top edge group 304a can operate in a drive mode when the bottom edge group 304b operates in a sense mode. In another example, every transducers within, for example, the top edge group 304a alternate between drive transducers and sense transducers. In other cases, each transducer can be operated in either a drive mode or a sense mode.

Figure 3B:
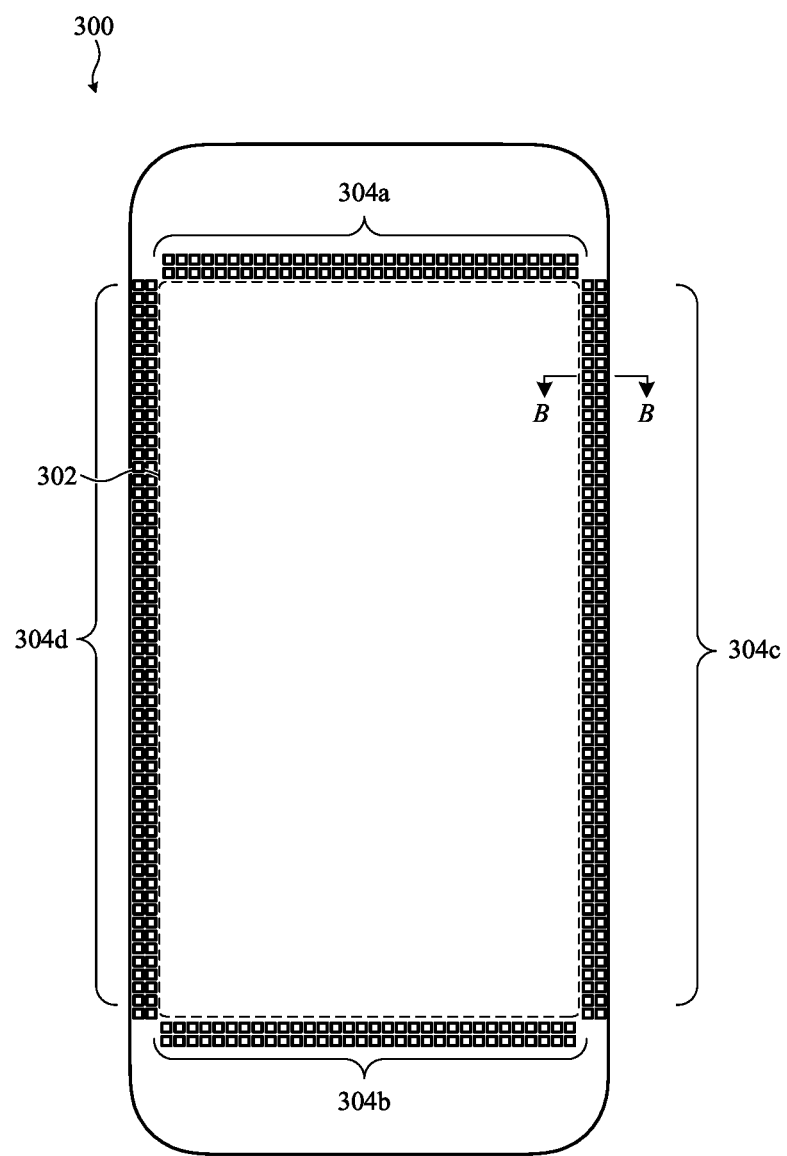
FIG. 3B depicts another distribution of transducers associated with an acoustic imaging system disposed on a bottom surface of a cover so as to circumscribe a substantially rectangular area.

Each of the top edge group 304a, the bottom edge group 304b, the right edge group 304c, and the left edge group 304d are illustrated as a single linear distribution of transducers, such a configuration is not required. For example, as shown in FIG. 3B, each of the top edge group 304a, the bottom edge group 304b, the right edge group 304c, and the left edge group 304d can be defined as include more than one adjacent linear distribution of transducers. In one embodiment, the outermost linear distribution of transducers may be configured to operate in a receive mode whereas the innermost linear distribution of transducers may be configured to operate in a drive mode.

Although FIG. 3B depicts each group as having two adjacent linear distributions of transducers, such a configuration is not required and other embodiments can include a larger number of adjacent linear distributions of transducers or a smaller number of adjacent linear distributions of transducers.

In still further embodiments, linear distributions of transducers need not be aligned with one another. For example, a second linear distribution may be offset with respect to a first linear distribution.

In still other examples, groups of transducers need not include the same number of transducers, the same distributions of transducers, or the same relative alignment of transducers.

Generally and broadly, FIGS. 4A-4F reference various example cross-sections of acoustic imaging systems such as described herein. It will be appreciated, however, that the depicted examples are not exhaustive; the various embodiments described with reference to FIGS. 4A-4F may be modified or combined in any number of suitable or implementation-specific ways.

Figure 4A:
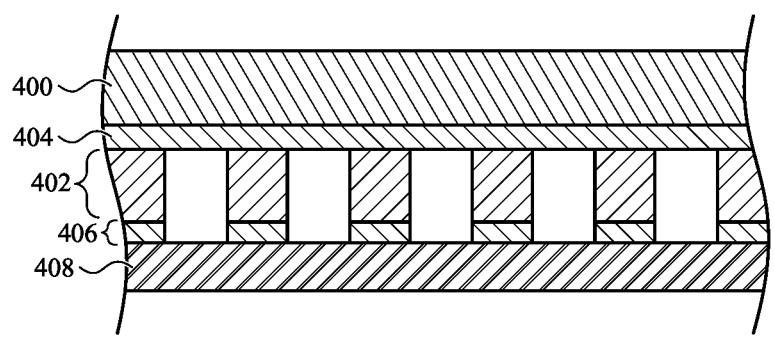
FIG. 4A depicts a simplified cross-section of a portion of an acoustic imaging system.

For example, FIG. 4A depicts a simplified cross-section of a portion of an acoustic imaging system, depicting several individual acoustic transducers coupled to a substrate 400. In one example, the acoustic transducers illustrated may be the acoustic transducers of the acoustic imaging system of FIG. 3A when viewed through section line A-A.

The illustrated embodiment depicts are six independent transducers 402 that share a shared electrode 404.

In certain embodiments, the shared electrode 404 can be a ground electrode, although this configuration is not required and can be, in certain embodiments, a voltage and/or power supply electrode. As illustrated, each of the independent transducers 402 are electrically coupled to the shared electrode 404. Each of the independent transducers 402 can be made from the same material, although this is not required; in some embodiments, different transducers can be made from different materials.

In some embodiments, the independent transducers 402 can be coupled to the shared electrode 404 by soldering. In some embodiments, the shared electrode 404 can be formed, layered, or otherwise disposed atop the independent transducers 402 in a manufacturing process. In some cases, the shared electrode 404 can be an optically transparent electrode, formed from a material such as indium tin oxide or metal nanowire.

In further embodiments, the independent transducers 402 can be coupled to the shared electrode 404 by an electrically conductive adhesive.

A series of individual electrodes, identified as the individual electrodes 406, electrically couple the independent transducers 402 to a sense/drive chip 408. The individual electrodes 406, the independent transducers 402, and the send/drive chip 408 are positioned adjacent to a bottom surface of the substrate 400a, and are coupled to a lower surface of the shared electrode 404.

The sense/drive chip 408 may be understood as the controller of other embodiments described and depicted herein, such as the controller 204 depicted in FIG. 2. The sense/drive chip 408 can be implemented as a circuit, as an integrated circuit, analog circuit, or as any combination thereof.

In some examples, the sense/drive chip 408 can be configured for both high voltage operation and low voltage operation, although such a configuration is not required of all embodiments. For example, in one embodiment, the sense/drive chip 408 is configured for high voltage driving of the independent transducers 402 and low voltage sensing of the independent transducers 402. In another embodiment, the sense/drive chip 408 is configured for low voltage driving and low voltage sensing. In still further embodiments, the sense/drive chip 408 is configured for both high voltage drive and high voltage sense.

In this manner, in some embodiments, the sense/drive chip 408 can be manufactured with both high-voltage-tolerant components and low-voltage-tolerant components. In many cases, low-voltage-tolerant components may be more sensitive to low voltage signals but may be damaged by high voltage signals. High-voltage-tolerant components may be less sensitive to low voltage signals (e.g., small changes in voltage), and therefore more sensitive to noise.

In such embodiments, the low-voltage-tolerant components can be protected from damage caused by high voltage using one or more isolation and/or voltage biasing methods. For example, in one embodiment, low-voltage-tolerant components can be physically isolated from high voltage via one or more switches enabled while high-voltage-tolerant components are operating.

In another embodiment, a ground node of the low-voltage-tolerant components can be biased upwardly while high-voltage-tolerant components are operating such that the potential difference between the low-voltage-tolerant components' ground and the high voltage required by the high-voltage-tolerant components is within the tolerance range of the low-voltage-tolerant components. Such a process is generally referred to herein as "ground shifting" of low-voltage-tolerant components.

When operating in a drive mode, the sense/drive chip 408 can provide a high voltage (e.g., 100 volts) signal to one or more of the independent electrodes 406 which can, in turn, excite the respective one or more independent transducers 402. In this mode, the largest potential difference between the sense/drive chip 408 and the shared electrode 404 can be a high voltage such as 103.3 volts (as one example). During this operation, low-voltage-tolerant components within the sense/drive chip 408 can be ground shifted to 100 volts. In this manner, the largest potential difference across low-voltage-tolerant components within the sense/drive chip 408 can be 3.3 volts (as one example).

In many cases, the sense/drive chip 408 can include one or more sense and drive circuits dedicated to each independent transducer 402. Conversely, certain embodiments may not include shared drive circuitry and/or shared sense circuitry.

Figure 4B:
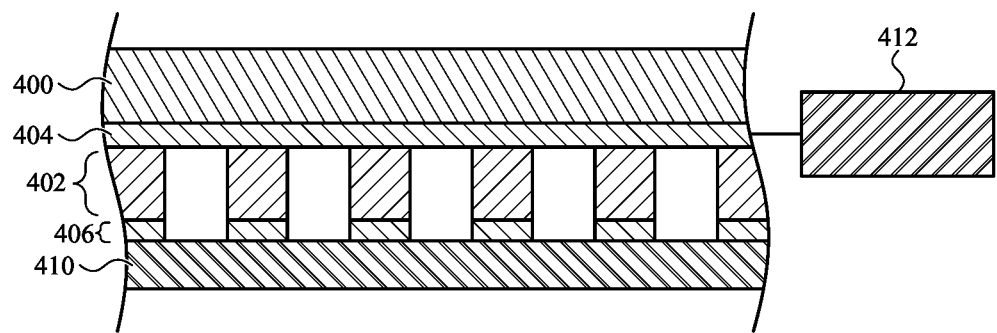
FIG. 4B depicts a simplified cross-section of a portion of another acoustic imaging system.

For example, as illustrated in FIG. 4B, a combination sense/drive chip may not be required. In this embodiment, the individual transducers 402 couple through the independent electrodes 406 directly to a sense chip 410. The individual transducers 402 couple through the shared electrode 404 directly to a drive chip 412. In these examples, individual transducers can be driven as a group and read individually. Such an embodiment can employ—should it be required by a particular implementation—ground shifting, isolation, or any other suitable means to protect low-voltage-tolerant components within the sense chip 410 from the high voltage generated during operation of the drive chip 412.

Figure 4C:
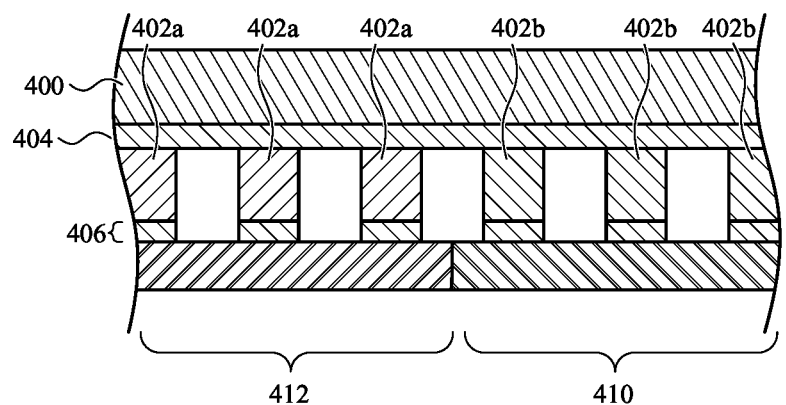
FIG. 4C depicts a simplified cross-section of a portion of yet another acoustic imaging system.

Still other embodiments are implemented in another manner. For example, as shown in FIG. 4C, a series of drive-mode transducers, identified as the drive-mode transducers 402a, can be separated from a corresponding series of sense-mode transducers, identified as the sense-mode transducers 402b. In one example, the acoustic transducers illustrated may be the acoustic transducers of the acoustic imaging system of FIG. 3B when viewed through section line B-B, with each linear distribution of transducers of the right edge group 304c representing three of either the drive-mode transducers 402a or the sense-mode transducers 402b depicted in FIG. 4C.

In this embodiment, the drive-mode transducers 402a and the sense-mode transducers 402b are coupled to the substrate 400 via the shared electrode 404. The drive-mode transducers 402a are coupled to a drive chip 412 and the sense-mode transducers 402b are coupled to a sense chip 410. The drive chip 412 and the sense chip 410 may be positioned adjacent to one another. In another embodiment, the drive chip 412 and the sense chip 410 can be different subcomponents or submodules of a single integrated circuit.

Figure 4D:
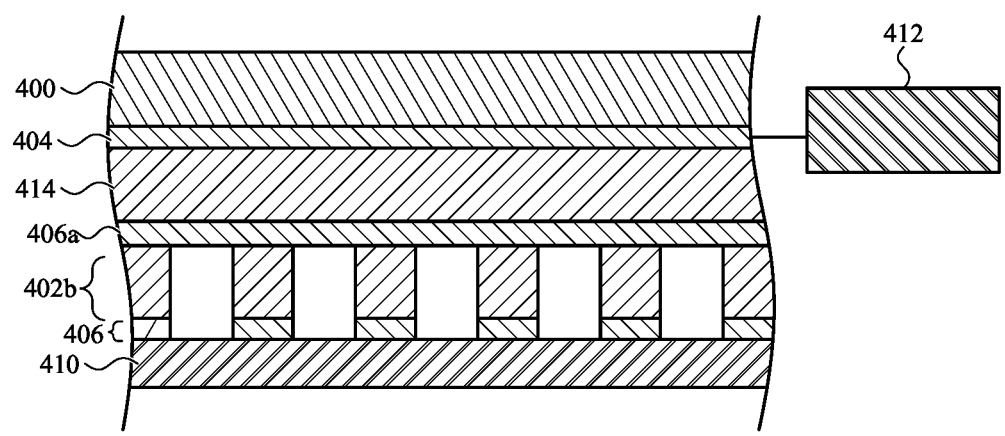
FIG. 4D depicts a simplified cross-section of a portion of yet another acoustic imaging system.

Still other embodiments are implemented in another manner. For example, as shown in FIG. 4D, a drive transducer 414 can be disposed over (e.g., vertically stacked) several sense-mode transducers, identified as the sense-mode transducers 402b. In some embodiments, the drive transducer 414 is formed from the same material as the sense-mode transducers 414, although this is not required. The drive transducer 414 is coupled to the sense-mode transducers 402b by a common electrode 406a. The sense-mode transducers 402b can be coupled to a sense chip 410 via individual electrodes 406b. The drive transducer 414 can be coupled to a drive chip 412. The sense chip 410 and the drive chip 412 can each be implemented as a circuit, as an integrated circuit, an analog circuit, or as any combination thereof. In other cases, sense-mode transducers can be stacked above the drive mode transducer.

As a result of this topology (including separate drive transducers and sense transducers), the sense-mode transducers 402b can operate separately from the drive-mode transducer 414. As a result, the sense-mode transducers 402b can begin receiving the moment the drive-mode transducer 414 is driven by the drive chip 412.

Figure 4E:
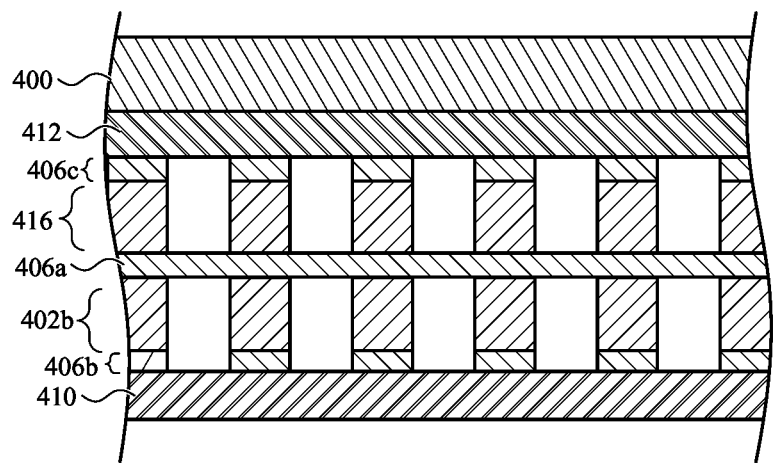
FIG. 4E depicts a simplified cross-section of a portion of yet another acoustic imaging system.

Still other embodiments are implemented in another manner. For example, as shown in FIG. 4E, a several drive-mode transducers, identified as the drive-mode transducers 416, can be disposed over (e.g., vertically stacked) several sense-mode transducers 402b. As with other embodiments described herein, the drive-mode transducers 416 may be the same material or may be a different material from the sense-mode transducers, identified as the sense-mode transducers 402b. In the illustrated embodiment, the drive-mode transducers 416 are coupled to the sense-mode transducers 402b by a common electrode 406a. In other embodiments, a common electrode is not required; individual electrodes can couple the drive-mode transducers 416 to the sense mode transducers 402b. The sense-mode transducers 402b can be coupled to a sense chip 410 via individual electrodes 406b. The drive transducer 414 can be coupled to a drive chip 412 via individual electrodes 406c. The sense chip 410 and the drive chip 412 can each be implemented as a circuit, as an integrated circuit, an analog circuit, or as any combination thereof. In other cases, the sense-mode transducers 402b can be stacked above the drive mode transducers.

As a result of this topology, and as with other embodiments described herein, the sense-mode transducers 402b can operate separately from the drive-mode transducer 414. As a result, the sense-mode transducers 402b can begin receiving the moment the drive-mode transducer 414 is driven by the drive chip 412.

Figure 4F:
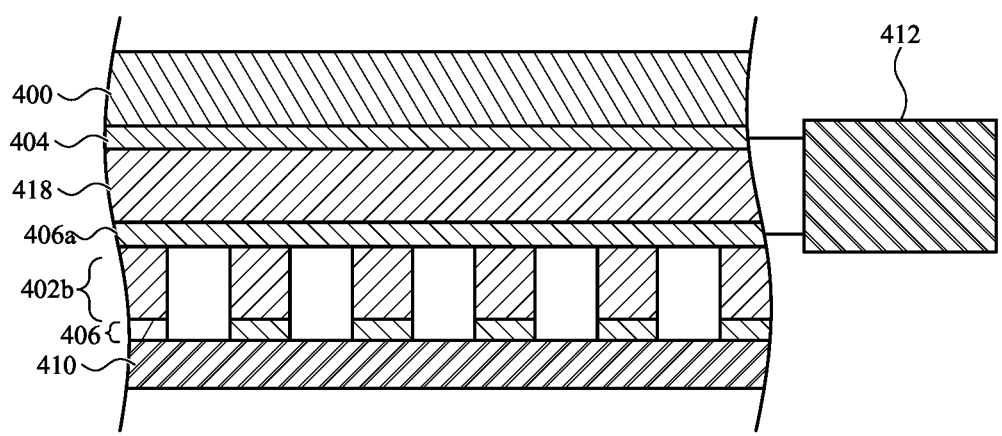
FIG. 4F depicts a simplified cross-section of a portion of yet another acoustic imaging system.

Still other embodiments are implemented in another manner. For example, as shown in FIG. 4F, a single drive-mode transducer sheet, identified as the drive-mode transducer 418, can be disposed over (e.g., vertically stacked) several sense-mode transducers, identified as the sense-mode transducers 402b. As with other embodiments described herein, the drive-mode transducer 418 may be the same material or may be a different material from the sense-mode transducers 402b. The drive-mode transducer 418 can be a single transducer, such as shown, or may be made up of a series of individual transducers, such as shown in FIG. 4E.

In many cases, the drive-mode transducer 418 is formed from a material selected for drive-mode power efficiency whereas the sense-mode transducers 402b can be formed from a material selected for sense-mode power efficiency (e.g., PVDF).

In one embodiment, the drive-mode transducer 418 is formed from one of a bulk PZT or a piezocomposite material. In some cases, a piezocomposite material (layers of piezoelectric materials separated by adhesive or epoxy) may be selected to increase the bandwidth of the drive-mode transducer 418 relative to a particular fundamental drive frequency. An increased drive bandwidth can increase the signal to noise ratio (e.g., reduced ringing).

In another embodiment, the drive-mode transducer 418 includes a backing. The backing may be a low-durometer adhesive or other resilient material. The backing can couple the drive-mode transducer 418 to another component, such as a supporting plate or frame. The backing serves to reduce and absorb reflections of the drive waveform that may reflect within the drive-mode transducer 418 as a result of an acoustic impedance mismatch between the drive-mode transducer 418 and the substrate 400, or the shared electrode 404.

In the illustrated embodiment, the drive-mode transducers 416 are coupled to the sense-mode transducers 402b by a common electrode 406a. In other embodiments, a common electrode is not required; individual electrodes can couple the drive-mode transducers 416 to the sense mode transducers 402b. The sense-mode transducers 402b can be coupled to a sense chip 410 via individual electrodes 406b. The drive transducer 414 can be coupled to a drive chip 412 via individual electrodes 406c. The sense chip 410 and the drive chip 412 can each be implemented as a circuit, as an integrated circuit, an analog circuit, or as any combination thereof. In other cases, the sense-mode transducers 402b can be stacked above the drive mode transducers. In this embodiment, as with the embodiment depicted in FIG. 4E, the drive chip 412, which may operate at high voltage, is separated and isolated from the sense chip 410, which may operate at low voltage. The common electrode 406a can be a ground reference for both the sense chip 410 and the drive chip 412. As a result of this topology, and as with other embodiments described herein, the sense-mode transducers 402b can operate separately from the drive-mode transducer 414. As a result, the sense-mode transducers 402b can begin receiving the moment the drive-mode transducer 414 is driven by the drive chip 412.

The foregoing embodiments depicted in FIGS. 4A-4F and the various alternatives thereof and variations thereto are presented, generally, for purposes of explanation, and to facilitate an understanding of various possible acoustic imaging system topologies. More specifically, FIGS. 4A-4F are presented to illustrate that transducers of an acoustic imaging system such as described herein can be configured to operate in both a drive mode and a sense mode, can be configured to operate in one of a drive mode or a sense mode, can be configured to operate in one of a drive mode or a sense mode. Further, the depicted embodiments are provided to facilitate an understanding that drive transducers may share one or more electrodes with sense electrodes, drive electrodes and sense electrodes may be formed from the same or different material, drive and sense electrodes may be segmented (e.g., pixelated) or unitary, drive or sense electrodes can be operated from the same silicon or from different silicon, drive chips can be integrated with or can be separate from sense chips, and so on. As such, it may be appreciated that the embodiments depicted in FIGS. 4A-4F are not intended to be exhaustive of all possible combinations, layouts, or topologies of drive electrodes, sense electrodes, drive transducers, sense transducers, multi-modal transducers, drive chips, sense chips, multimodal chips, and so on. Instead, the depicted examples are understood to be merely a subset of the representative embodiments of an acoustic imaging system such as described herein that may be implemented within the spirit and scope of this disclosure.

Figure 5A:
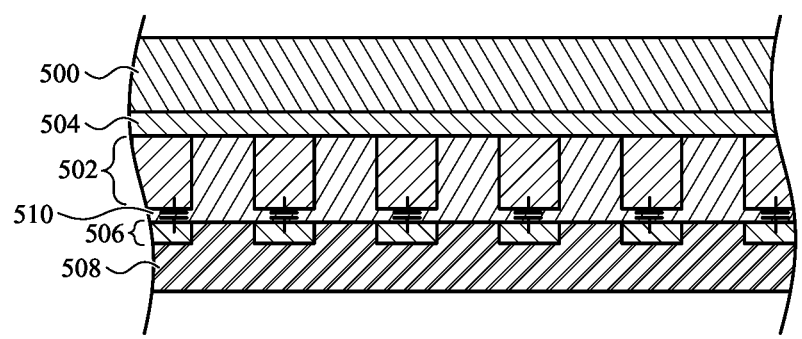
FIG. 5A depicts a simplified cross-section of a portion of an acoustic imaging system that may be configured for capacitive signaling, drive, and/or sense.
Figure 5B:
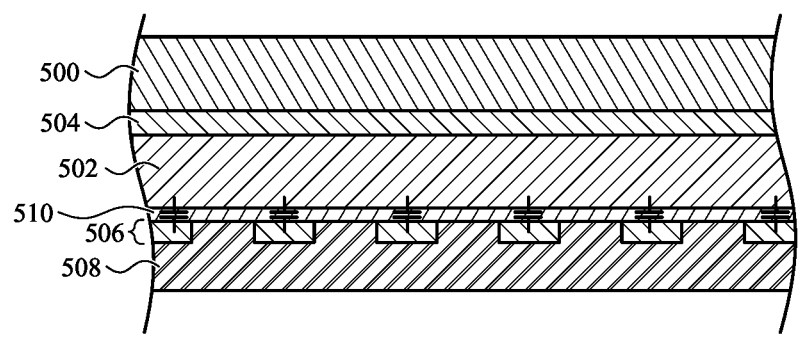
FIG. 5B depicts a simplified cross-section of a portion of another acoustic imaging system that may be configured for capacitive signaling, drive, and/or sense.

Generally and broadly, FIGS. 5A-5B reference various example cross-sections of acoustic imaging systems such as described herein that may be capacitively driven and/or capacitively read. It will be appreciated, however, that the depicted examples are not exhaustive; the various embodiments described with reference to FIGS. 5A-5B may be modified or combined in any number of suitable or implementation-specific ways.

For example, FIG. 5A depicts a simplified cross-section of a portion of an acoustic imaging system, depicting several individual acoustic transducers coupled to a substrate 500. In one example, the acoustic transducers illustrated may be the acoustic transducers of the acoustic imaging system of FIG. 3A when viewed through section line A-A.

Similar to the embodiments depicted in FIGS. 4A-4F, the illustrated embodiment depicts are six independent transducers 502 that share a shared electrode 504. It is appreciated however, that this configuration may not be required. For example, a single electrode may be used, such as shown in FIG. 5B.

In certain embodiments, the shared electrode 504 can be a ground electrode, although this configuration is not required and can be, in certain embodiments, a voltage and/or power supply electrode. As illustrated, each of the independent transducers 502 are electrically coupled to the shared electrode 504. Each of the independent transducers 502 can be made from the same material, although this is not required; in some embodiments, different transducers can be made from different materials.

In some embodiments, the independent transducers 502 can be coupled to the shared electrode 504 by soldering. In some embodiments, the shared electrode 504 can be formed, layered, or otherwise disposed atop the independent transducers 502 in a manufacturing process. In some cases, the shared electrode 504 can be an optically transparent electrode, formed from a material such as indium tin oxide or metal nanowire. In further embodiments, the independent transducers 502 can be coupled to the shared electrode 504 by an electrically conductive adhesive.

A series of individual electrodes, identified as the individual electrodes 506 extend from a sense/drive chip 508. The sense/drive chip 508 may be understood as the controller of other embodiments described and depicted herein, such as the controller 204 depicted in FIG. 2. The sense/drive chip 508 can be implemented as a circuit, as an integrated circuit, analog circuit, or as any combination thereof.

As with other embodiments described herein, the sense/drive chip 508 can be configured for both high voltage operation and low voltage operation, although such a configuration is not required of all embodiments. For example, in one embodiment, the sense/drive chip 508 is configured for high voltage driving of the independent transducers 502 and low voltage sensing of the independent transducers 502. In another embodiment, the sense/drive chip 508 is configured for low voltage driving and low voltage sensing. In still further embodiments, the sense/drive chip 508 is configured for both high voltage drive and high voltage sense.

The individual electrodes 506 are separated from the independent transducers 502 by a dielectric material 510. In these examples, the dielectric material 510 is disposed to encapsulate the independent electrodes 502. In some cases, the dielectric material 510 may be an adhesive, a layer deposited via vapor deposition, an epoxy, or any other suitable layer. In many embodiments, the dielectric material 510 has a high dielectric constant and is disposed as a thin layer.

As a result of this configuration, the individual electrodes 506 each form a capacitor with one respective transducer. As a result, the operation of driving the transducers can be modeled as a circuit including a capacitor having a very large capacitance inserted between a voltage source (e.g., drive chip) and a transducer (e.g., individual transducer). Similarly, the operation of reading the transducers can be modeled as a circuit including a capacitor having a very large capacitance inserted between a voltage source (e.g., individual transducer) and a sense circuit (e.g., sense chip). As may be appreciated, such a configuration can be more easily and efficiently manufactured at scale; precise alignment and precise electrical connection between electrodes and transducers may not be required.

As with the embodiments depicted in FIGS. 4A-4F, the foregoing embodiments depicted in FIGS. 5A-5B and the various alternatives thereof and variations thereto are presented, generally, for purposes of explanation, and to facilitate an understanding of various possible acoustic imaging system topologies that incorporate capacitive signaling, capacitive drive, and/or capacitive sense. As such, it may be appreciated that the embodiments depicted in FIGS. 5A-5B are not intended to be exhaustive of all possible combinations, layouts, or topologies of drive electrodes, sense electrodes, drive transducers, sense transducers, multi-modal transducers, drive chips, sense chips, multimodal chips, and so on that incorporate capacitive signaling, drive, or sense topologies. Instead, the depicted examples are understood to be merely a subset of the representative embodiments of an acoustic imaging system such as described herein that may be implemented within the spirit and scope of this disclosure. Particularly, it may be understood that any embodiment described herein, including those embodiments depicted in FIGS. 4A-4F, can be implemented with capacitive signaling, drive, or sense topologies.

As noted with respect to many embodiments described herein, acoustic imaging systems can be implemented in a number of ways, many of which may depend upon the electronic device which incorporates such a system. For example, in some examples, a single controller can be configured to drive and read each transducer of a particular acoustic imaging system. In other examples, multiple controllers can be used.

Figure 6A:
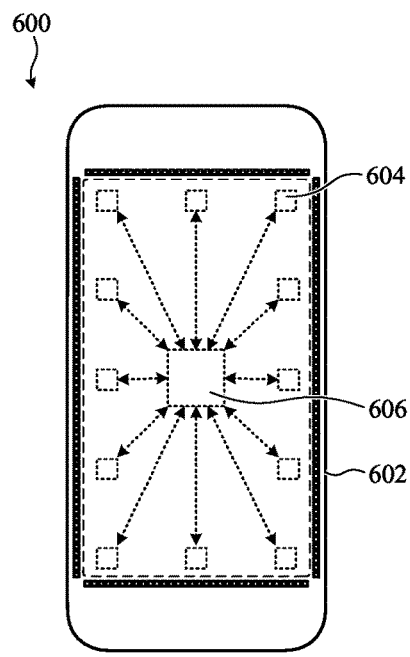
FIG. 6A depicts an acoustic imaging system implemented with a distributed controller.
Figure 6B:
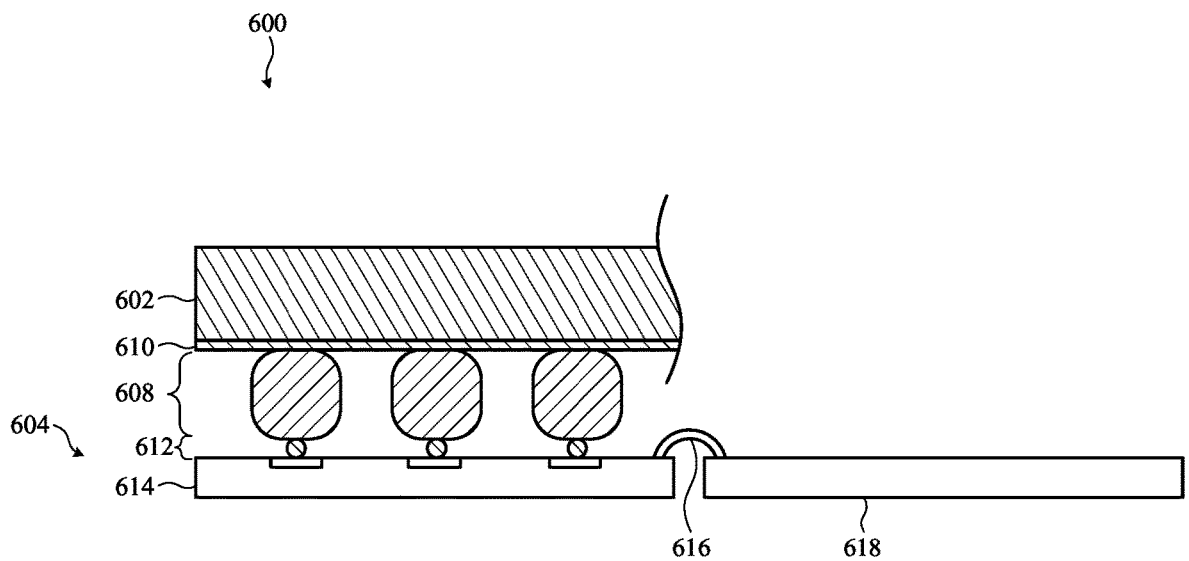
FIG. 6B depicts a simplified cross-section of a portion of an acoustic imaging system implemented with a distributed controller.

Generally and broadly, FIGS. 6A-6B reference an acoustic imaging system incorporating multiple controllers and/or a distributed controller system. It will be appreciated, however, that the depicted examples are not exhaustive; the various embodiments described with reference to FIGS. 6A-6B may be modified or combined in any number of suitable or implementation-specific ways.

For example, FIG. 6A depicts an electronic device 600 incorporating an acoustic imaging system such as described herein. As with other embodiments, the electronic device 600 includes a substrate 602. The acoustic imaging system is coupled to a lower surface of the substrate 602.

As with other embodiments described herein, the acoustic imaging system includes a controller. In the illustrated embodiment, the controller is implemented with a series of subgroup controllers, one of which is labeled as the subgroup controller 604 and the master controller 606. As illustrated, the series of subgroup controllers are communicably coupled to the master controller 606 in a hub-and-spoke configuration, although this is not required.

In this example, the subgroup controller 604 is associated with a subgroup of transducers nearby or adjacent to the subgroup controller 604. Similarly, other subgroup controllers of the series of subgroup controllers are each associated with a respective one subgroup of transducers. More specifically, the subgroup controller 604 may be purpose-configured to drive and/or read only certain transducers of the acoustic imaging system.

In this example, the master controller 606 couples to, and coordinates the actions of, each subgroup controller of the series of subgroup controllers, including the subgroup controller 204.

A subgroup controller 204 can be implemented in any number of suitable ways. In certain embodiments, a subgroup controller can be implemented as a combination of individual purpose-configured circuits that are, directly or indirectly, communicably coupled to one another. For example, one example configuration is shown in FIG. 6B. In this embodiment, a series of acoustic transducers 608 are coupled, via a common electrode 610, to the underside of the substrate 602. An opposite side of the series of acoustic transducers 608 is coupled, via a series of electrical contacts 612 (or via capacitive signaling through a dielectric material, to a first section 614 of the subgroup controller.

In many examples, the first section 614 can include one or more analog or digital circuits configured to facilitate driving or sensing of the series of the acoustic transducers 608. For example, in one embodiment, the first section 614 is a thin-film transistor substrate strip that includes at least one amplification stage. The amplification stage can serve as a pre-amp for signals obtained when reading one or more of the series of acoustic transducers 608. In this example, the first section 614 can be manufactured in a time and cost-efficient manner.

In another example, the first section 614 can be made from a flexible circuit. The flexible circuit can include at least one amplification stage such as described above. In other cases, other circuits and/or purpose configured circuit topologies can be included such as, but not limited to: addressing circuits (e.g., shift registers), power control or regulation circuits, drive circuits, switch circuits, filtering circuits, multi-stage amplification circuits, analog-to-digital conversion stages and/or circuits, encryption and/or decryption circuits, compression circuits, data streaming or protocol conformity circuits, and so on. In still further embodiments, the first section 614 may be implemented without circuitry; the first section 614 may be a passive interposer.

In certain embodiments, the first section 614 can couple, via an interposer 616 (or other suitable connection) to a second section 618. The second section 618 can be an integrated circuit that is purpose-configured for driving and/or reading the series of acoustic transducers 608 via the first section 614. In this manner, by separating certain functions of the subgroup controller 204 into a first section 614 and a second section 618 manufacturing and signal processing efficiency can be improved. As with the first section 614, the second section 618 can include other circuits and/or purpose configured circuit topologies can be included such as, but not limited to: addressing circuits (e.g., shift registers), power consumption regulation circuits, drive circuits, switch circuits, filtering circuits, multi-stage amplification circuits, analog-to-digital conversion stages and/or circuits, encryption and/or decryption circuits, compression circuits, data streaming or protocol conformity circuits, and so on.

The foregoing embodiments depicted in FIGS. 6A-6B and the various alternatives thereof and variations thereto are presented, generally, for purposes of explanation, and to facilitate an understanding of various possible methods for dividing and/or distributing the processing and/or signal conditioning load of an acoustic imaging system such as described herein. Instead, the depicted examples are understood to be merely a subset of the representative embodiments of an acoustic imaging system such as described herein that may be implemented within the spirit and scope of this disclosure.

Figure 7:
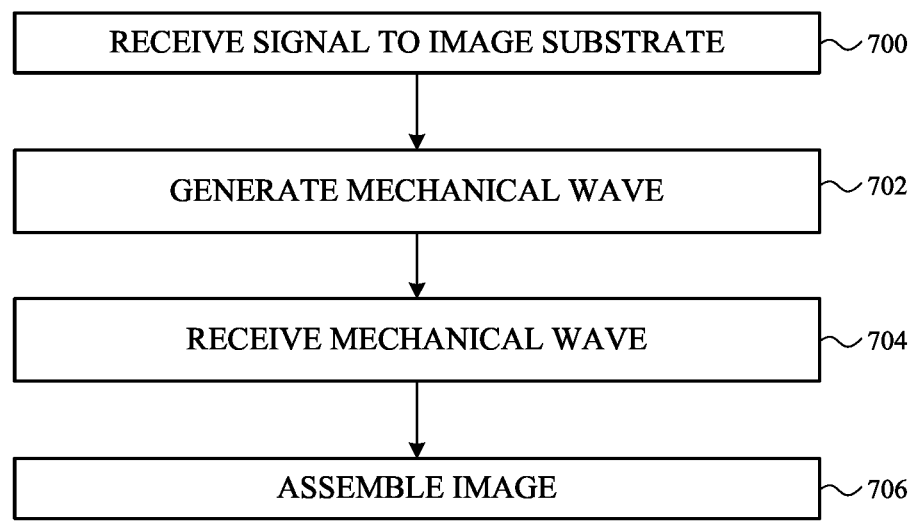
FIG. 7 depicts example operations of a method of operating an acoustic imaging system.

FIG. 7 depicts example operations of a simplified method of operating an acoustic imaging system of an electronic device. The method begins at operation 700 in which an acoustic imaging system receives a signal (e.g., from an electronic device processor) to assemble an image of a substrate to which the acoustic imaging system is coupled. At operation 702, a mechanical wave is generated within the substrate. Next, at operation 704, a mechanical wave is received. Finally, at operation 704, data associated with the mechanical wave received at operation 704 is used to generate an image of an object in physical contact with the substrate.

In some cases, the image may be used as touch input to an electronic device. In other cases, the image may be used to authenticate a function, operation or task of the electronic device. In still further cases, the image may be used to determine an amount of force applied to the electronic device.

Many embodiments of the foregoing disclosure may include or may be described in relation to various methods of operation, use, manufacture, and so on. Notably, the operations of methods presented herein are meant only to be exemplary and, accordingly, are not necessarily exhaustive. For example an alternate operation order or fewer or additional steps may be required or desired for particular embodiments.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not meant to be exhaustive or to limit the embodiments to the precise forms disclosed. It will be apparent to one of ordinary skill in the art that many modifications and variations are possible in view of the above teachings. In particular, any features described with respect to one embodiment may also be used in some embodiments, where compatible. Likewise, the features of the different embodiments may be exchanged, substituted, or omitted where compatible and appropriate.

The present disclosure recognizes that personal information data, including biometric data, in the present technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data, which benefit the user, are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric data. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

What is claimed is:

1. An acoustic imaging sensor comprising:
a first distribution of transducers circumscribing a portion of a substrate and operable in a drive mode in which at least one transducer of the first distribution of transducers mechanically deforms in response to a drive signal;
a second distribution of transducers disposed adjacent to the first distribution of transducers and operable in a sense mode in which at least one transducer of the second distribution of transducers produces an electronic signal when a section of the substrate adjacent to the at least one transducer of the second distribution of transducers mechanically deforms;
a master controller configured to:
actuate a first subgroup controller to cause the at least one transducer of the first distribution of transducers to cause a mechanical wave to be generated across at least one of a top surface or a thickness of the substrate toward an interior portion of the substrate; and
receive, from a second subgroup controller, the electronic signal from the at least one transducer of the second distribution of transducers; and an image resolver in communication with the master controller and operable to construct an image of an object engaging the top surface of the substrate based on the electronic signal received by the master controller.

2. The acoustic imaging sensor of claim 1, wherein the master controller comprises:
a drive circuit configured to generate the drive signal; and
a sense circuit configured to receive the electronic signal.

3. The acoustic imaging sensor of claim 1, wherein each transducer of the first distribution of transducers and the second distribution of transducers is coupled to a bottom surface of the substrate.

4. The acoustic imaging sensor of claim 1, wherein the first distribution of transducers is arranged as a row positioned adjacent to a rectilinear edge of the substrate.

5. The acoustic imaging sensor of claim 4, wherein the second distribution of transducers is arranged as a second row positioned adjacent to the first distribution of transducers.

6. The acoustic imaging sensor of claim 4, wherein the second distribution of transducers is arranged interstitially with the first distribution of transducers.

7. The acoustic imaging sensor of claim 1, wherein the first distribution of transducers is arranged as a series of parallel rows aligned adjacent to a rectilinear edge of the substrate.

8. The acoustic imaging sensor of claim 7, wherein the second distribution of transducers is arranged as a second series of parallel rows aligned parallel to the first distribution of transducers.

9. The acoustic imaging sensor of claim 7, wherein the second distribution of transducers is vertically aligned with the first distribution of transducers.

10. An electronic device comprising:
a housing;
a display disposed at least partially within the housing;
a transparent cover positioned over the display;
an acoustic imaging sensor coupled to a bottom surface of the transparent cover, the acoustic imaging sensor comprising,
a first distribution of transducers circumscribing the transparent cover and operable in a drive mode in which at least one transducer of the first distribution of transducers mechanically deforms in response to a drive signal;
a second distribution of transducers disposed adjacent to the first distribution of transducers and operable in a sense mode in which at least one transducer of the second distribution of transducers produces an electronic signal when a section of the transparent cover adjacent to the at least one transducer of the second distribution of transducers mechanically deforms;
a master controller configured to:
actuate a first subgroup controller to cause the at least one transducer of the first distribution of transducers to cause a mechanical wave to be generated across at least one of a top surface or a thickness of the transparent cover toward an interior portion of the transparent cover; and
receive, from a second subgroup controller, the electronic signal from the at least one transducer of the second distribution of transducers; and
an image resolver in communication with the master controller and operable to construct an image of an object engaging the top surface of the transparent cover based on the electronic signal received by the master controller.

11. The electronic device of claim 10, wherein the master controller comprises:
a drive circuit configured to generate the drive signal; and
a sense circuit configured to receive the electronic signal.

12. The electronic device of claim 10, wherein each transducer of the first distribution of transducers and the second distribution of transducers is coupled to a bottom surface of the transparent cover.

13. The electronic device of claim 10, wherein the first distribution of transducers is arranged as a row positioned adjacent to a rectilinear edge of the transparent cover.

14. The electronic device of claim 13, wherein the second distribution of transducers is arranged as a second row positioned adjacent to the first distribution of transducers.

15. The electronic device of claim 13, wherein the second distribution of transducers is arranged interstitially with the first distribution of transducers.

16. The electronic device of claim 10, wherein the first distribution of transducers is arranged as a series of parallel rows aligned adjacent to a rectilinear edge of the transparent cover.

17. The electronic device of claim 16, wherein the second distribution of transducers is arranged as a second series of parallel rows aligned parallel to the first distribution of transducers.

18. The electronic device of claim 16, wherein the second distribution of transducers is vertically aligned with the first distribution of transducers.

* * * * *